US006843998B1

(12) United States Patent
Steward et al.

(10) Patent No.: US 6,843,998 B1
(45) Date of Patent: Jan. 18, 2005

(54) METHODS AND COMPOSITIONS FOR THE TREATMENT OF PANCREATITIS

(75) Inventors: Lance E. Steward, Irvine, CA (US); George Sachs, Encino, CA (US); Kei Roger Aoki, Coto de Caza, CA (US)

(73) Assignee: Allergan, Inc., Irvine, CA (US)

( * ) Notice: Subject to any disclaimer, the term of this patent is extended or adjusted under 35 U.S.C. 154(b) by 0 days.

(21) Appl. No.: 09/548,409

(22) Filed: Apr. 13, 2000

Related U.S. Application Data

(63) Continuation-in-part of application No. 09/288,326, filed on Apr. 8, 1999.

(51) Int. Cl.[7] ................................................ A61K 39/02

(52) U.S. Cl. ............................... 424/236.1; 424/247.1; 424/197.11; 424/198.1

(58) Field of Search .......................... 424/236.1, 247.1, 424/197.11, 198.1

(56) References Cited

U.S. PATENT DOCUMENTS 5,919,665 A 7/1999 Williams et al.

FOREIGN PATENT DOCUMENTS

| | | |
|---|---|---|
| WO | 91/00725 | 1/1991 |
| WO | WO 95/32738 | 12/1995 |
| WO | WO 96/33273 | 10/1996 |
| WO | WO 98/07864 | 2/1998 |

OTHER PUBLICATIONS

Tani et al, "Effect of a New Cholecystokinin Receptor Antagonist Loxiglumide on Acute Pancreatitis in Two Experimental Animal Models", Pancreas 5: pp. 284–290 (1990).
Rizo et al, "Mechanics of membrane fusion", Nature Structural Biology 5: pp. 839–842 (Oct. 1998).
Niemann et al, "Clostridial neurotoxins: new tools for dissecting exocytosis", Trends in Cell Biology 4: pp. 179–185(May 1994).
Coffield et al, "The Site and Mechanism of Action of Botulinum Neurotoxin in Therapy with Botulinum Toxin", Neurological Disease and Therapy, Therapy with Botulinum Toxin, pp. 3–13 (1994).
Tonello et al, "Tetanus and Botulism Neurotoxins in Intracellular Protein Catabolism", Adv. Exp. Med. Biol. 389, pp. 251–260 (1996).
Sharma et al, "Hemagglutinin Binding Mediated Protection of Botulinum Neurotoxin From Proteolysis", Journal of Natural Toxins 7: pp. 239–253(1998).
Kennedy et al, Identification of Two Amino Acids of the Human Cholecystokin–A Receptor That Interact with the N–terminal Moiety of Cholecystokinin, The Journal of Biological Chemistry, 272: pp. 2920–2926 (1997).

Pohl et al, "Ligand–induced Internalization of Cholecystokinin Receptors", The Journal of Biological Chemistry 272: pp. 18179–18184 (1997).
Ji et al, "Direct Identification of a Distinct Site of Interaction between the Carboxyl–terminal Residue of Cholecystokinin and the Type A Cholecystokinin Receptor Using Photoaffinity Labeling", The Journal of Biological Chemistry 272, pp. 24393–24401 (1997).

Jagerschmidt et al, "Mutation of $Asp^{100}$ in the Second Transmembrane Domain of the Cholecystokinin B Receptor Increases Antagonist Binding and Reduces Signal Transduction",Molecular Pharmacology 48: pp. 783–789(1995).

Zhou et al, "Expression and Purification of the Light Chain of Botulinum Neurotoxin A: A Single Mutation Abolishes Its Cleavage of SNAP–25 and Neurotoxicity after Reconstitution with the Heavy Chain, Biochemistry" 34: pp. 15175–15181 (1995).

Kurazono et al, "Minimal Essential Domains Specifying Toxicity of the Light Chains of Tetanus Toxin and Botulinum Neurotoxin Type A*", The Journal of Biologcal Chemistry, pp. 14721–14729 (1992).

Oblatt–Montal et al, "Formation of ions channels in lipid bilayers by a peptide with predicted transmembrane sequence of botulinum neurotoxin A", Protein Science, vol. 4: pp. 1490–1497(1995).

Ulrich et al, "Molecular cloning and functional expression of the human gallbladder cholecystokinin A receptor", Gen Bank 416772, Web site ncbi.nlm.nih.gov.

Binz et al, "The complete sequence of the botulinum type A neurotoxin and its comparison with other Clostridial neurotoxins", Gen Bank M30196, Web Site ncbi.nlm.nih.gov.

Sharma et al, "Functional role of Hn–33; Enhanced cleavage of synaptic protein SNAP–25 b botulinum neurotoxin A and E", Database Chemabs 'Online', XP–002154380 (Abstract) Book of Abstracts, 216$^{th}$ ACS National Meeting, Boston, Aug. 23–27 (1998).

Fujita–Yoshigaki et al, "Vesicle–associated membrane protein 2 is essential for cAMP–regulated exocytosis in rat parotid acinar cells. The inhibition of cAMP–dependent amylase release by botulinum neurotoxin B", XP–002154378(Abstract) J. Biol. Chem. (1996), 271(22) 13130–13134.

*Primary Examiner*—Patrick J. Nolan
(74) *Attorney, Agent, or Firm*—Dean G. Stathakis; Carlos A. Fisher; Martin A. Voet

(57) ABSTRACT

Methods and compositions for the treatment of acute pancreatitis in a mammal. Particular compositions comprise a binding element, a translocation element, and a therapeutic element able to prevent accumulation of digestive enzymes within the pancreas.

10 Claims, No Drawings

SEQUENCE LISTING

<160> NUMBER OF SEQ ID NOS: 12

<210> SEQ ID NO 1
<211> LENGTH: 129
<212> TYPE: PRT
<213> ORGANISM: Homo sapiens

<400> SEQUENCE: 1

```
Ser Glu Gln Glu Asn Cys Glu Leu Ile Ser Thr Ile Asn Gly Met Asn
 1               5                  10                  15

Ser Gly Val Cys Leu Cys Val Leu Met Ala Val Leu Ala Ala Gly Ala
             20                  25                  30

Leu Thr Gln Pro Val Pro Pro Ala Asp Pro Ala Gly Ser Gly Leu Gln
         35                  40                  45

Arg Ala Glu Glu Ala Pro Arg Arg Gln Leu Arg Val Ser Gln Arg Thr
     50                  55                  60

Asp Gly Glu Ser Arg Ala His Leu Gly Ala Leu Leu Ala Arg Tyr Ile
 65                  70                  75                  80

Gln Gln Ala Arg Lys Ala Pro Ser Gly Arg Met Ser Ile Val Lys Asn
                 85                  90                  95

Leu Gln Asn Leu Asp Pro Ser His Arg Ile Ser Asp Arg Asp Tyr Met
             100                 105                 110

Gly Trp Met Asp Phe Gly Arg Arg Ser Ala Glu Glu Tyr Glu Tyr Pro
         115                 120                 125

Ser
```

<210> SEQ ID NO 2
<211> LENGTH: 58
<212> TYPE: PRT
<213> ORGANISM: Homo sapiens

<400> SEQUENCE: 2

Val Ser Gln Arg Thr Asp Gly Glu Ser Arg Ala His Leu Gly Ala Leu

```
                1               5                  10                  15
Leu Ala Arg Tyr Ile Gln Gln Ala Arg Lys Ala Pro Ser Gly Arg Met
                20                  25                  30

Ser Ile Val Lys Asn Leu Gln Asn Leu Asp Pro Ser His Arg Ile Ser
                35                  40                  45

Asp Arg Asp Tyr Met Gly Trp Met Asp Phe
                50                  55

<210> SEQ ID NO 3
<211> LENGTH: 39
<212> TYPE: PRT
<213> ORGANISM: Homo sapiens

<400> SEQUENCE: 3

Tyr Ile Gln Gln Ala Arg Lys Ala Pro Ser Gly Arg Met Ser Ile Val
  1               5                  10                  15

Lys Asn Leu Gln Asn Leu Asp Pro Ser His Arg Ile Ser Asp Arg Asp
                20                  25                  30

Tyr Met Gly Trp Met Asp Phe
                35

<210> SEQ ID NO 4
<211> LENGTH: 33
<212> TYPE: PRT
<213> ORGANISM: Homo sapiens

<400> SEQUENCE: 4

Lys Ala Pro Ser Gly Arg Met Ser Ile Val Lys Asn Leu Gln Asn Leu
  1               5                  10                  15

Asp Pro Ser His Arg Ile Ser Asp Arg Asp Tyr Met Gly Trp Met Asp
                20                  25                  30

Phe

<210> SEQ ID NO 5
<211> LENGTH: 12
<212> TYPE: PRT
<213> ORGANISM: Homo sapiens

<400> SEQUENCE: 5

Ile Ser Asp Arg Asp Tyr Met Gly Trp Met Asp Phe
  1               5                  10

<210> SEQ ID NO 6
<211> LENGTH: 9
<212> TYPE: PRT
<213> ORGANISM: Homo sapiens

<400> SEQUENCE: 6

Arg Asp Tyr Met Gly Trp Met Asp Phe
  1               5

<210> SEQ ID NO 7
<211> LENGTH: 448
<212> TYPE: PRT
<213> ORGANISM: Clostridium botulinum

<400> SEQUENCE: 7

Met Pro Phe Val Asn Lys Gln Phe Asn Tyr Lys Asp Pro Val Asn Gly
  1               5                  10                  15

Val Asp Ile Ala Tyr Ile Lys Ile Pro Asn Ala Gly Gln Met Gln Pro
                20                  25                  30
```

-continued

```
Val Lys Ala Phe Lys Ile His Asn Lys Ile Trp Val Ile Pro Glu Arg
         35                  40                  45
Asp Thr Phe Thr Asn Pro Glu Glu Gly Asp Leu Asn Pro Pro Glu
 50                  55                  60
Ala Lys Gln Val Pro Val Ser Tyr Tyr Asp Ser Thr Tyr Leu Ser Thr
 65                  70                  75                  80
Asp Asn Glu Lys Asp Asn Tyr Leu Lys Gly Val Thr Lys Leu Phe Glu
                 85                  90                  95
Arg Ile Tyr Ser Thr Asp Leu Gly Arg Met Leu Leu Thr Ser Ile Val
                 100                 105                 110
Arg Gly Ile Pro Phe Trp Gly Gly Ser Thr Ile Asp Thr Glu Leu Lys
             115                 120                 125
Val Ile Asp Thr Asn Cys Ile Asn Val Ile Gln Pro Asp Gly Ser Tyr
             130                 135                 140
Arg Ser Glu Glu Leu Asn Leu Val Ile Gly Pro Ser Ala Asp Ile
145                 150                 155                 160
Ile Gln Phe Glu Cys Lys Ser Phe Gly His Glu Val Leu Asn Leu Thr
                 165                 170                 175
Arg Asn Gly Tyr Gly Ser Thr Gln Tyr Ile Arg Phe Ser Pro Asp Phe
             180                 185                 190
Thr Phe Gly Phe Glu Glu Ser Leu Glu Val Asp Thr Asn Pro Leu Leu
             195                 200                 205
Gly Ala Gly Lys Phe Ala Thr Asp Pro Ala Val Thr Leu Ala His Glu
         210                 215                 220
Leu Ile His Ala Gly His Arg Leu Tyr Gly Ile Ala Ile Asn Pro Asn
225                 230                 235                 240
Arg Val Phe Lys Val Asn Thr Asn Ala Tyr Tyr Glu Met Ser Gly Leu
                 245                 250                 255
Glu Val Ser Phe Glu Glu Leu Arg Thr Phe Gly Gly His Asp Ala Lys
             260                 265                 270
Phe Ile Asp Ser Leu Gln Glu Asn Glu Phe Arg Leu Tyr Tyr Tyr Asn
             275                 280                 285
Lys Phe Lys Asp Ile Ala Ser Thr Leu Asn Lys Ala Lys Ser Ile Val
         290                 295                 300
Gly Thr Thr Ala Ser Leu Gln Tyr Met Lys Asn Val Phe Lys Glu Lys
305                 310                 315                 320
Tyr Leu Leu Ser Glu Asp Thr Ser Gly Lys Phe Ser Val Asp Lys Leu
                 325                 330                 335
Lys Phe Asp Lys Leu Tyr Lys Met Leu Thr Glu Ile Tyr Thr Glu Asp
             340                 345                 350
Asn Phe Val Lys Phe Lys Val Leu Asn Arg Lys Thr Tyr Leu Asn
             355                 360                 365
Phe Asp Lys Ala Val Phe Lys Ile Asn Ile Val Pro Lys Val Asn Tyr
         370                 375                 380
Thr Ile Tyr Asp Gly Phe Asn Leu Arg Asn Thr Asn Leu Ala Ala Asn
385                 390                 395                 400
Phe Asn Gly Gln Asn Thr Glu Ile Asn Asn Met Asn Phe Thr Lys Leu
                 405                 410                 415
Lys Asn Phe Thr Gly Leu Phe Glu Phe Tyr Lys Leu Leu Cys Val Arg
             420                 425                 430
Gly Ile Ile Thr Ser Lys Thr Lys Ser Leu Asp Lys Gly Tyr Asn Lys
         435                 440                 445
```

<210> SEQ ID NO 8
<211> LENGTH: 423
<212> TYPE: PRT
<213> ORGANISM: Clostridium botulinum

<400> SEQUENCE: 8

```
Ala Leu Asn Asp Leu Cys Ile Lys Val Asn Trp Asp Leu Phe Phe
  1               5                  10                  15

Ser Pro Ser Glu Asp Asn Phe Thr Asn Asp Leu Asn Lys Gly Glu Glu
                 20                  25                  30

Ile Thr Ser Asp Thr Asn Ile Glu Ala Glu Glu Asn Ile Ser Leu
         35                  40                  45

Asp Leu Ile Gln Gln Tyr Tyr Leu Thr Phe Asn Phe Asp Asn Glu Pro
 50                  55                  60

Glu Asn Ile Ser Ile Glu Asn Leu Ser Ser Asp Ile Ile Gly Gln Leu
 65                  70                  75                  80

Glu Leu Met Pro Asn Ile Glu Arg Phe Pro Asn Gly Lys Lys Tyr Glu
                 85                  90                  95

Leu Asp Lys Tyr Thr Met Phe His Tyr Leu Arg Ala Gln Glu Phe Glu
                100                 105                 110

His Gly Lys Ser Arg Ile Ala Leu Thr Asn Ser Val Asn Glu Ala Leu
            115                 120                 125

Leu Asn Pro Ser Arg Val Tyr Thr Phe Phe Ser Ser Asp Tyr Val Lys
130                 135                 140

Lys Val Asn Lys Ala Thr Glu Ala Ala Met Phe Leu Gly Trp Val Glu
145                 150                 155                 160

Gln Leu Val Tyr Asp Phe Thr Asp Glu Thr Ser Glu Val Ser Thr Thr
                165                 170                 175

Asp Lys Ile Ala Asp Ile Thr Ile Ile Pro Tyr Ile Gly Pro Ala
            180                 185                 190

Leu Asn Ile Gly Asn Met Leu Tyr Lys Asp Asp Phe Val Gly Ala Leu
            195                 200                 205

Ile Phe Ser Gly Ala Val Ile Leu Leu Glu Phe Ile Pro Glu Ile Ala
210                 215                 220

Ile Pro Val Leu Gly Thr Phe Ala Leu Val Ser Tyr Ile Ala Asn Lys
225                 230                 235                 240

Val Leu Thr Val Gln Thr Ile Asp Asn Ala Leu Ser Lys Arg Asn Glu
                245                 250                 255

Lys Trp Asp Glu Val Tyr Lys Tyr Ile Val Thr Asn Trp Leu Ala Lys
            260                 265                 270

Val Asn Thr Gln Ile Asp Leu Ile Arg Lys Lys Met Lys Glu Ala Leu
            275                 280                 285

Glu Asn Gln Ala Glu Ala Thr Lys Ala Ile Ile Asn Tyr Gln Tyr Asn
290                 295                 300

Gln Tyr Thr Glu Glu Glu Lys Asn Asn Ile Asn Phe Asn Ile Asp Asp
305                 310                 315                 320

Leu Ser Ser Lys Leu Asn Glu Ser Ile Asn Lys Ala Met Ile Asn Ile
                325                 330                 335

Asn Lys Phe Leu Asn Gln Cys Ser Val Ser Tyr Leu Met Asn Ser Met
            340                 345                 350

Ile Pro Tyr Gly Val Lys Arg Leu Glu Asp Phe Asp Ala Ser Leu Lys
        355                 360                 365

Asp Ala Leu Leu Lys Tyr Ile Tyr Asp Asn Arg Gly Thr Leu Ile Gly
370                 375                 380
```

```
Gln Val Asp Arg Leu Lys Asp Lys Val Asn Asn Thr Leu Ser Thr Asp
385                 390                 395                 400

Ile Pro Phe Gln Leu Ser Lys Tyr Val Asp Asn Gln Arg Leu Leu Ser
                405                 410                 415

Thr Phe Thr Glu Tyr Ile Lys
            420

<210> SEQ ID NO 9
<211> LENGTH: 382
<212> TYPE: PRT
<213> ORGANISM: Clostridium botulinum

<400> SEQUENCE: 9

Gln Leu Phe Asn Leu Glu Ser Ser Lys Ile Glu Val Ile Leu Lys Asn
1               5                   10                  15

Ala Ile Val Tyr Asn Ser Met Tyr Glu Asn Phe Ser Thr Ser Phe Trp
                20                  25                  30

Ile Arg Ile Pro Lys Tyr Phe Asn Ser Ile Ser Leu Asn Asn Glu Tyr
            35                  40                  45

Thr Ile Ile Asn Cys Met Glu Asn Asn Ser Gly Trp Lys Val Ser Leu
    50                  55                  60

Asn Tyr Gly Glu Ile Ile Trp Thr Leu Gln Asp Thr Gln Glu Ile Lys
65                  70                  75                  80

Gln Arg Val Val Phe Lys Tyr Ser Gln Met Ile Asn Ile Ser Asp Tyr
                85                  90                  95

Ile Asn Arg Trp Ile Phe Val Thr Ile Thr Asn Asn Arg Leu Asn Asn
            100                 105                 110

Ser Lys Ile Tyr Ile Asn Gly Arg Leu Ile Asp Gln Lys Pro Ile Ser
        115                 120                 125

Asn Leu Gly Asn Ile His Ala Ser Asn Asn Ile Met Phe Lys Leu Asp
    130                 135                 140

Gly Cys Arg Asp Thr His Arg Tyr Ile Trp Ile Lys Tyr Phe Asn Leu
145                 150                 155                 160

Phe Asp Lys Glu Leu Asn Glu Lys Glu Ile Lys Asp Leu Tyr Asp Asn
                165                 170                 175

Gln Ser Asn Ser Gly Ile Leu Lys Asp Phe Trp Gly Asp Tyr Leu Gln
            180                 185                 190

Tyr Asp Lys Pro Tyr Tyr Met Leu Asn Leu Tyr Asp Pro Asn Lys Tyr
        195                 200                 205

Val Asp Val Asn Asn Val Gly Ile Arg Gly Tyr Met Tyr Leu Lys Gly
    210                 215                 220

Pro Arg Gly Ser Val Met Thr Thr Asn Ile Tyr Leu Asn Ser Ser Leu
225                 230                 235                 240

Tyr Arg Gly Thr Lys Phe Ile Ile Lys Lys Tyr Ala Ser Gly Asn Lys
                245                 250                 255

Asp Asn Ile Val Arg Asn Asn Asp Arg Val Tyr Ile Asn Val Val Val
            260                 265                 270

Lys Asn Lys Glu Tyr Arg Leu Ala Thr Asn Ala Ser Gln Ala Gly Val
        275                 280                 285

Glu Lys Ile Leu Ser Ala Leu Glu Ile Pro Asp Val Gly Asn Leu Ser
    290                 295                 300

Gln Val Val Val Met Lys Ser Lys Asn Asp Gln Gly Ile Thr Asn Lys
305                 310                 315                 320

Cys Lys Met Asn Leu Gln Asp Asn Asn Gly Asn Asp Ile Gly Phe Ile
```

```
                    325                 330                 335
        Gly Phe His Gln Phe Asn Asn Ile Ala Lys Leu Val Ala Ser Asn Trp
                    340                 345                 350

Tyr Asn Arg Gln Ile Glu Arg Ser Ser Arg Thr Leu Gly Cys Ser Trp
                    355                 360                 365

Glu Phe Ile Pro Val Asp Asp Gly Trp Gly Glu Arg Pro Leu
                    370                 375                 380

<210> SEQ ID NO 10
<211> LENGTH: 4835
<212> TYPE: DNA
<213> ORGANISM: Clostridium botulinum

<400> SEQUENCE: 10
aagcttctaa atttaaatta ttaagtataa atccaaataa acaatatgtt caaaaacttg      60
atgaggtaat aatttctgta ttagataata tggaaaaata tatagatata tctgaagata     120
atagattgca actaatagat aacaaaaata acgcaaagaa gatgataatt agtaatgata     180
tatttatttc caattgttta accctatctt ataacggtaa atatatatgt ttatctatga     240
aagatgaaaa ccataattgg atgatatgta ataatgatat gtcaaagtat ttgtatttat     300
ggtcatttaa ataattaata atttaattaa ttttaaatat tataagaggt gttaaatatg     360
ccatttgtta ataaacaatt taattataaa gatcctgtaa atggtgttga tattgcttat     420
ataaaaattc caaatgcagg acaaatgcaa ccagtaaaag cttttaaaat tcataataaa     480
atatgggtta ttccagaaag agatacattt acaaatcctg aagaaggaga tttaaatcca     540
ccaccagaag caaacaagt tccagtttca tattatgatt caacatattt aagtacagat     600
aatgaaaaag ataattattt aaagggagtt acaaaattat tgagagaat ttattcaact     660 gatcttggaa gaatgttgtt aacatcaata gtaaggggaa taccattttg gggtggaagt     720
acaatagata cagaattaaa agttattgat actaattgta ttaatgtgat acaaccagat     780
ggtagttata gatcagaaga acttaatcta gtaataatag gaccctcagc tgatattata     840
cagtttgaat gtaaaagctt tggacatgaa gttttgaatc ttacgcgaaa tggttatggc     900
tctactcaat acattagatt tagcccagat tttacatttg gttttgagga gtcacttgaa     960
gttgatacaa atcctctttt aggtgcaggc aaatttgcta cagatccagc agtaacatta    1020
gcacatgaac ttatacatgc tggacataga ttatatggaa tagcaattaa tccaaatagg    1080 gttttttaaag taaatactaa tgcctattat gaaatgagtg ggttagaagt aagctttgag    1140
gaacttagaa catttggggg acatgatgca agtttatag atagtttaca ggaaaacgaa    1200
tttcgtctat attattataa taagtttaaa gatatagcaa gtacacttaa taagctaaa    1260 tcaatagtag gtactactgc ttcattacag tatatgaaaa atgttttaa agagaaatat    1320 ctcctatctg aagatacatc tggaaaattt cggtagata aattaaaatt tgataagtta    1380
tacaaaatgt taacagagat ttacacagag gataattttg ttaagttttt taagtactt    1440 aacagaaaaa catatttgaa ttttgataaa gccgtattta agataaatat agtacctaag    1500
gtaaattaca caatatatga tggatttaat ttaagaaata caaatttagc agcaaacttt    1560
aatggtcaaa atacagaaat taataatatg aatttttacta aactaaaaa ttttactgga    1620 ttgtttgaat tttataagtt gctatgtgta agagggataa taacttctaa aactaaatca    1680
ttagataaag gatacaataa ggcattaaat gatttatgta tcaaagtaa taattgggac    1740 ttgtttttta gtccttcaga agataatttt actaatgatc taaataaagg agaagaaatt    1800
```

```
acatctgata ctaatataga agcagcagaa gaaaatatta gtttagattt aatacaacaa      1860
tattatttaa cctttaattt tgataatgaa cctgaaaata tttcaataga aaatctttca      1920
agtgacatta taggccaatt agaacttatg cctaatatag aaagatttcc taatggaaaa      1980
aagtatgagt tagataaata tactatgttc cattatcttc gtgctcaaga atttgaacat      2040
ggtaaatcta ggattgcttt aacaaattct gttaacgaag cattattaaa tcctagtcgt      2100
gtttatacat ttttttcttc agactatgta aagaaagtta ataaagctac ggaggcagct      2160 atgttttag gctgggtaga acaattagta tatgatttta ccgatgaaac tagcgaagta       2220
agtactacgg ataaaattgc ggatataact ataattattc catatatagg acctgcttta      2280
aatataggta atatgttata taaagatgat tttgtaggtg ctttaatatt ttcaggagct      2340
gttattctgt tagaatttat accagagatt gcaatacctg tattaggtac ttttgcactt      2400
gtatcatata ttgcgaataa ggttctaacc gttcaaacaa tagataatgc tttaagtaaa      2460
agaaatgaaa aatgggatga ggtctataaa tatatagtaa caaattggtt agcaaaggtt      2520
aatacacaga ttgatctaat aagaaaaaaa atgaagaag ctttagaaaa tcaagcagaa       2580
gcaacaaagg ctataataaa ctatcagtat aatcaatata ctgaggaaga gaaaaataat      2640 attaattta atattgatga tttaagttcg aaacttaatg agtctataaa taaagctatg       2700
attaatataa ataaatttt gaatcaatgc tctgtttcat atttaatgaa ttctatgatc       2760
ccttatggtg ttaaacggtt agaagatttt gatgctagtc ttaaagatgc attattaaag      2820
tatatatatg ataatagagg aactttaatt ggtcaagtag atagattaaa agataaagtt      2880
aataatacac ttagtacaga tatacctttt cagctttcca aatacgtaga taatcaaaga      2940
ttattatcta catttactga atatattaag aatattatta atacttctat attgaattta      3000
agatatgaaa gtaatcattt aatagactta tctaggtatg catcaaaaat aaatattggt      3060
agtaaagtaa attttgatcc aatagataaa aatcaaattc aattatttaa tttagaaagt      3120
agtaaaattg aggtaatttt aaaaaatgct attgtatata atagtatgta tgaaaatttt      3180
agtactagct tttggataag aattcctaag tattttaaca gtataagtct aaataatgaa      3240
tatacaataa taaattgtat ggaaaataat tcaggatgga agtatcact taattatggt       3300 gaaataatct ggactttaca ggatactcag gaaataaaac aaagagtagt ttttaaatac      3360
agtcaaatga ttaatatatc agattatata aacagatgga ttttttgtaac tatcactaat     3420 aatagattaa ataactctaa aatttatata aatggaagat taatagatca aaaaccaatt      3480
tcaaatttag gtaatattca tgctagtaat aatataatgt ttaaattaga tggttgtaga      3540
gatacacata gatatatttg gataaaaatat tttaatctttt ttgataagga attaaatgaa    3600
aaagaaatca aagatttata tgataatcaa tcaaattcag gtatttttaaa agacttttgg    3660 ggtgattatt tacaatatga taaaccatac tatatgttaa atttatatga tccaaataaa      3720
tatgtcgatg taaataatgt aggtattaga ggttatatga tcttaaagg gcctagaggt       3780 agcgtaatga ctacaaacat ttatttaaat tcaagtttgt ataggggac aaaatttatt       3840 ataaaaaaat atgcttctgg aaataaagat aatattgtta gaataatga tcgtgtatat       3900 attaatgtag tagttaaaaa taaagaatat aggttagcta ctaatgcatc acaggcaggc      3960
gtagaaaaaa tactaagtgc attagaaata cctgatgtag gaaatctaag tcaagtagta     4020
gtaatgaagt caaaaaatga tcaaggaata acaaataaat gcaaaatgaa tttacaagat     4080
aataatggga atgatatagg ctttatagga tttcatcagt ttaataatat agctaaacta      4140
gtagcaagta attggtataa tagacaaata gaaagatcta gtaggacttt gggttgctca      4200
```

-continued

```
tgggaattta ttcctgtaga tgatggatgg ggagaaaggc cactgtaatt aatctcaaac    4260
tacatgagtc tgtcaagaat tttctgtaaa catccataaa aattttaaaa ttaatatgtt    4320
taagaataac tagatatgag tattgtttga actgcccctg tcaagtagac aggtaaaaaa    4380
ataaaaatta agatactatg gtctgatttc gatattctat cggagtcaga ccttttaact    4440
tttcttgtat ccttttgta ttgtaaaact ctatgtattc atcaattgca agttccaatt    4500
agtcaaaatt atgaaacttt ctaagataat acatttctga ttttataatt tcccaaaatc    4560
cttccatagg accattatca atacatctac caactcgaga catactttga gttgcgccta    4620
tctcattaag tttattcttg aaagatttac ttgtatattg aaaaccgcta tcactgtgaa    4680
aaagtggact agcatcagga ttggaggtaa ctgctttatc aaaggtttca aagacaagga    4740
cgttgttatt tgattttcca agtacatagg aaataatgct attatcatgc aaatcaagta    4800
tttcactcaa gtacgccttt gtttcgtctg ttaac                              4835
```

<210> SEQ ID NO 11
<211> LENGTH: 15
<212> TYPE: PRT
<213> ORGANISM: Homo sapiens

<400> SEQUENCE: 11

Glu Pro Lys Ser Cys Asp Lys Thr His Thr Cys Pro Pro Cys Pro
1               5                   10                  15

<210> SEQ ID NO 12
<211> LENGTH: 5
<212> TYPE: PRT
<213> ORGANISM: Artificial Sequence
<220> FEATURE:
<221> NAME/KEY: METAL
<222> LOCATION: (3)...(4)
<223> OTHER INFORMATION: Xaa=Ala,Cys,Asp,Glu,Phe,Gly,His,Ile,Lys,Leu,
      Met,Asn,Pro,Gln,Arg,Ser,Thr,Val,Trp orTyr
<220> FEATURE:
<223> OTHER INFORMATION: Generic Clostridial zinc binding domain

<400> SEQUENCE: 12

His Glu Xaa Xaa His
1               5

METHODS AND COMPOSITIONS FOR THE TREATMENT OF PANCREATITIS

This application is a continuation-in-part of application Ser. No. 09/288,326, filed Apr. 8, 1999.

FIELD OF THE INVENTION

The present invention includes methods and compositions for the treatment of acute pancreatitis. In a preferred embodiment the invention concerns the use of agents to reduce or prevent the secretion of pancreatic digestive enzymes within the pancreas. Such agents are targeted to pancreatic cells, and serve to prevent the exocytotic fusion of vesicles containing these enzymes with the plasma membrane. The invention is also concerned with methods of treating a mammal suffering from pancreatitis through the administration of such agents.

BACKGROUND OF THE INVENTION

Pancreatitis is a serious medical condition involving an inflammation of the pancreas. In acute or chronic pancreatitis the inflammation manifests itself in the release and activation of pancreatic enzymes within the organ itself, leading to autodigestion. In many cases of acute pancreatitis, the condition can lead to death.

In normal mammals, the pancreas, a large gland similar in structure to the salivary gland, is responsible for the production and secretion of digestive enzymes, which digest ingested food, and bicarbonate for the neutralization of the acidic chyme produced in the stomach. The pancreas contains acinar cells, responsible for enzyme production, and ductal cells, which secrete large amounts of sodium bicarbonate solution. The combined secretion product is termed "pancreatic juiced"; this liquid flows through the pancreatic duct past the sphincter of Oddi into the duodenum. The secretion of pancreatic juice is stimulated by the presence of chyme in the upper portions of the small intestine, and the precise composition of pancreatic juice appears to be influenced by the types of compounds (carbohydrate, lipid, protein, and/or nucleic acid) in the chyme.

The constituents of pancreatic juice includes proteases (trypsin, chymotrypsin, carboxypolypeptidase), nucleases (RNAse and DNAse), pancreatic amylase, and lipases (pancreatic lipase, cholesterol esterase and phospholipase). Many of these enzymes, including the proteases, are initially synthesized by the acinar cells in an inactive form as zymogens: thus trypsin is synthesized as trypsinogen, chymotrypsin as chymotypsinogen, and carboxypolypeptidase as procarboxypolypeptidase. These enzymes are activated according to a cascade, wherein, in the first step, trypsin is activated through proteolytic cleavage by the enzyme enterokinase. Trypsinogen can also be autoactivated by trypsin; thus one activation has begun, the activation process can proceed rapidly. Trypsin, in turn, activates both chymotypsinogen and procarboxypolypeptidase to form their active protease counterparts.

The enzymes are normally activated only when they enter the intestinal mucosa in order to prevent autodigestion of the pancreas. In order to prevent premature activation, the acinar cells also co-secrete a trypsin inhibitor that normally prevents activation of the proteolytic enzymes within the secretory cells and in the ducts of the pancreas. Inhibition of trypsin activity also prevents activation of the other proteases.

Pancreatitis can occur when an excess amount of trypsin saturates the supply of trypsin inhibitor. This, in turn, can be caused by underproduction of trypsin inhibitor, or the overabundance of trypsin within the cells or ducts of the pancreas. In the latter case, pancreatic trauma or blockage of a duct can lead to localized overabundance of trypsin; under acute conditions large amounts of pancreatic zymogen secretion can pool in the damaged areas of the pancreas. If even a small amount of free trypsin is available activation of all the zymogenic proteases rapidly occurs, and can lead to digestion of the pancreas (acute pancreatitis) and in particularly severe cases to the patient's death.

Pancreatic secretion is normally regulated by both hormonal and nervous mechanisms. When the gastric phase of stomach secretion occurs, parasympathetic nerve impulses are relayed to the pancreas, which initially results in acetylcholine release, followed by secretion of enzymes into the pancreatic acini for temporary storage.

When acid chyme thereafter enters the small intestine, the mucosal cells of the upper intestine release a hormone called secretin. In humans, secretin is a 27 amino acid (3400 Dalton) polypeptide initially produced as the inactive form prosecretin, which is then activated by proteolytic cleavage. Secretin is then absorbed into the blood. Secretin causes the pancreas to secrete large quantities of a fluid containing bicarbonate ion. Secretin does not stimulate the acinar cells, which produce the digestive enzymes. The bicarbonate fluid serves to neutralize the chyme and to provide a slightly alkaline optimal environment for the enzymes.

Another peptide hormone, cholecystokinin (CCK) is released by the mucosal cells in response to the presence of food in the upper intestine. As described in further detail below, human CCK is synthesized as a protoprotein of 115 amino acids. Active CCK forms are quickly taken into the blood through the digestive tract, and normally stimulate the secretion of enzymes by the acinar cells. However, stimulation of the CCK receptor by the CCK analogs cerulein and CCK-octapeptide (CCK-8) appears to lead to a worsening of morbidity and mortality in mammals in whom pancreatitis is induced. See Tani et al., *Pancreas* 5:284–290 (1990).

As indicated above, the digestive enzymes are synthesized as zymogens; proto-enzyme synthesis occurs in the rough endoplasmic reticulum of the acinar cells. The zymogens are then packaged within vesicles having a single lipid bilayer membrane. The zymogens are packed within the vesicles so densely that they appear as quasi-crystalline structures when observed under light microscopy and the zymogen granules are electron-dense when observed under the electron microscope. The vesicles are localized within the cytoplasm of the acinar cells. Secretion of zymogens by the acinar cells occurs through vesicle docking and subsequent fusion with the plasma membrane, resulting in the liberation of the contents into the extracellular milieu.

Nerve cells appear to secrete neurotransmitters and other intercellular signaling factors through a mechanism of membrane fusion that is shared with other cell types, see e.g., Rizo & Sudhof, *Nature Struct. Biol.* 5:839–842 (October 1998), hereby incorporated by reference herein, including the pancreatic acinar cells.

Although the Applicants do not wish to be bound by theory, it is believed that a vesicle first contacts the intracellular surface of the cellular membrane in a reaction called docking. Following the docking step the membrane fuses with and becomes part of the plasma membrane through a series of steps that currently remain relatively uncharacterized, but which clearly involve certain vesicle and membrane-associated proteins, as has been illustrated using neural models.

In neurons, neurotransmitters are packaged within synaptic vesicles, formed within the cytoplasm, then transported to the inner plasma membrane where the vesicles dock and fuse with the plasma membrane. Recent studies of nerve cells employing clostridial neurotoxins as probes of membrane fusion have revealed that fusion of synaptic vesicles with the cell membrane in nerve cells depends upon the presence of specific proteins that are associated with either the vesicle or the target membrane. See id. These proteins have been termed SNAREs. As discussed in further detail below, a protein alternatively termed synaptobrevin or VAMP (vesicle-associated membrane protein) is a vesicle-associated SNARE (v-SNARE). There are at least two isoforms of synaptobrevin; these two isoforms are differentially expressed in the mammalian central nervous system, and are selectively associated with synaptic vesicles in neurons and secretory organelles in neuroendocrine cells. The target membrane-associated SNAREs (t-SNARES) include syntaxin and SNAP-25. Following docking, the VAMP protein forms a core complex with syntaxin and SNAP-25; the formation of the core is complex appears to be an essential step to membrane fusion. See Rizo & Sudhof, id. and Neimmann et al., *Trends in Cell Biol.* 4:179–185 (May 1994), hereby incorporated by referenced herein.

Recently evidence has increasingly indicated that the SNARE system first identified in neural cells is a general model for membrane fusion in eukaryotic cells. A yeast exocytotic core complex similar to that of the synaptic vesicles of mammalian neural cells has been characterized, and found to contain three proteins: Sso 1 (syntaxin 1 homolog), SncI (synaptobrevin homolog), and sec9 (SNAP-25 homolog). Rizo & Sudhof, id. These proteins share a high degree of amino acid sequence homology with their mammalian synaptosomal counterparts.

All mammalian non-neuronal cells appear to contain cellubrevin, a synaptobrevin analog—this protein is involved in the intracellular transport of vesicles, and is cleaved by TeTx, BoNT/E, BoNT/F, and BoNT/G. Homologs of syntaxin have been identified in yeast (e.g., sso1p and sso2p) and mammalian non-neuronal cells (syn2p, syn3p, syn4p and syn5p). Finally, as indicated above, a yeast SNAP-25 homolog, sec9 has been identified; this protein appears to essential for vesicle fusion with the plasma membrane.

Intoxication of neural cells by clostridial neurotoxins exploits specific characteristics of the SNARE proteins. These neurotoxins, most commonly found expressed in *Clostridium botulinum* and *Clostridium tetanus*, are highly potent and specific poisons of neural cells. These Gram positive bacteria secrete two related but distinct toxins, each comprising two disulfide-linked amino acid chains: a light chain (L) of about 50 KDa and a heavy chain (H) of about 100 KDa, which are wholly responsible for the symptoms of botulism and tetanus, respectively.

The tetanus and botulinum toxins are among the most lethal substances known to man; both toxins function by inhibiting neurotransmitter release in affected neurons. The tetanus neurotoxin (TeNT) acts mainly in the central nervous system, while botulinum neurotoxin (BoNT) acts at the neuromuscular junction; both toxins inhibit acetylcholine release from the nerve terminal of the affected neuron into the synapse, resulting in paralysis or reduced target organ function.

The tetanus neurotoxin (TeNT) is known to exist in one immunologically distinct type; the botulinum neurotoxins (BoNT) are known to occur in seven different immunologically distinct serotypes, termed BoNT/A through BoNT/G. While all of these latter types are produced by isolates of *C. botulinum*, two other species, *C. baratii* and *C. butyricum* also produce toxins similar to /F and /E, respectively. See e.g., Coffield et al., *The Site and Mechanism of Action of Botulinum Neurotoxin in Therapy with Botulinum Toxin* 3–13 (Jankovic J. & Hallett M. eds. 1994), the disclosure of which is incorporated herein by reference.

Regardless of type, the molecular mechanism of intoxication appears to be similar. In the first step of the process, the toxin binds to the presynaptic membrane of the target neuron through a specific interaction between the heavy chain and a neuronal cell surface receptor; the receptor is thought to be different for each type of botulinum toxin and for TeNT. The carboxy terminal (C-terminal) half of the heavy chain is required for targeting of the toxin to the cell surface. The cell surface receptors, while not yet conclusively identified, appear to be distinct for each neurotoxin serotype.

In the second step, the toxin crosses the plasma membrane of the poisoned cell. The toxin is first engulfed by the cell through receptor-mediated endocytosis, and an endosome containing the toxin is formed. The toxin (or light chain thereof) then escapes the endosome into the cytoplasm of the cell. This last step is thought to be mediated by the amino terminal (N-terminal) half of the heavy chain, which triggers a conformational change of the toxin in response to a pH of about 5.5 or lower. Endosomes are known to possess a proton pump that decreases intra-endosomal pH. The conformational shift exposes hydrophobic residues in the toxin, which permits the toxin to embed itself in the endosomal membrane. The toxin then translocates through the endosomal membrane into the cytosol.

Either during or after translocation the disulfide bond joining the heavy and light chain is reduced, and the light chain is released into the cytoplasm. The entire toxic activity of botulinum and tetanus toxins is contained in the light chain of the holotoxin; the light chain is a zinc (Zn++) endopeptidase which selectively cleaves the SNARE proteins essential for recognition and docking of neurotransmitter-containing vesicles with the cytoplasmic surface of the plasma membrane, and fusion of the vesicles with the plasma membrane. The light chain of TxNT, BoNT/B, BoNT/D, BoNT/F, and BoNT/G cause specific proteolysis of VAMP, an integral protein. During proteolysis, most of the VAMP present at the cytosolic surface of the synaptic vesicle is inactivated as a result of any one of these cleavage events. Each toxin cleaves a different specific peptide bond.

BoNT/A and /E selectively cleave the plasma membrane-associated SNARE protein SNAP-25; this protein is bound to and present on the cytoplasmic surface of the plasma membrane. BoNT/C1 cleaves syntaxin, which exists as an integral protein having most of its mass exposed to the cytosol. Syntaxin interacts with the calcium channels at presynaptic terminal active zones. See Tonello et al., *Tetanus and Botulism Neurotoxins in Intracellular Protein Catabolism* 251–260 (Suzuki K & Bond J. eds. 1996), the disclosure of which is incorporated by reference as part of this specification. Bo/NTC1 also appears to cleave SNAP-25.

Both TeNT and BoNT are specifically taken up by cells present at the neuromuscular junction. BoNT remains within peripheral neurons and, as indicated above, blocks release of the neurotransmitter acetylcholine from these cells.

By contrast TeNT, through its receptor, enters vesicles that move in a retrograde manner along the axon to the soma, and is discharged into the intersynaptic space between motor neurons and the inhibitory neurons of the spinal cord. At this point, TeNT binds receptors of the inhibitory neurons, is again internalized, and the light chain enters the cytosol to block the release of the inhibitory neurotransmitters 4-aminobutyric acid (GABA) and glycine from these cells. Id.

International Patent Publication No. WO 96/33273 relates to derivatives of botulinum toxin designed to prevent neurotransmitter release from sensory afferent neurons to treat chronic pain. Such derivatives are targeted to nociceptive neurons using a targeting moiety that binds to a binding site of the surface of the neuron.

International Patent Publication No. 98/07864 discusses the production of recombinant toxin fragments that have domains that enable the polypeptide to translocate into a target cell or which increase the solubility of the polypeptide, or both.

SUMMARY OF THE INVENTION

The present invention concerns methods and compositions useful for the treatment of acute pancreatitis. This condition is largely due to the defective secretion of zymogen granules by acinar cells, and by the premature co-mingling of the secreted zymogens with lysosomal hydrolysates capable of activating trypsin, thereby triggering the protease activation cascade and resulting in the destruction of pancreatic tissue.

In one embodiment of this aspect, the invention is a therapeutic agent comprising a chimeric protein containing an amino acid sequence-specific endopeptidase activity which will specifically cleave at least one synaptic vesicle-associated protein selected from the group consisting of SNAP-25, syntaxin or VAMP, in combination with the translocation activity of the N-terminus of a clostridial neurotoxin heavy chain, wherein the chimeric protein further comprises a recognition domain which will bind a human cholecystokinin (CCK) receptor. Upon binding of the recognition domain of the protein to the CCK receptor, the protein is specifically transported into cells containing CCK receptors (pancreatic acinar cells) through receptor-mediated endocytosis. In a preferred embodiment, the CCK receptor is the CCK A receptor.

Once inside the acinar cell, the chimeric protein functions in a manner similar to that of a clostridial neurotoxin within its target neuron. The toxin moiety is translocated from the endosome into the cytoplasm, where it acts to cleave a SNARE protein identical or homologous to SNAP-25, syntaxin or VAMP. The cleavage of this protein prevents formation of a core complex between the SNARE proteins and thus prevents or reduces the extent of fusion of the vesicle with the target membrane. This, in turn, results in inhibition of zymogen release from the acinar cells and of zymogen activation by lysosomal hydrolases. The autodigestion of pancreatic tissue in acute pancreatitis is therefore reduced or eliminated.

Another embodiment of the present invention concerns a method of treating a patient suffering from acute pancreatitis by administering an effective amount of such a chimeric protein.

Another embodiment of the invention concerns a therapeutic composition that contains the translocation activity of a clostridial neurotoxin heavy chain in combination with a recognition domain able to bind a specific cell type and a therapeutic element having an activity other than the endopeptidase activity of a clostridial neurotoxin light chain.

A non-exclusive list of certain such therapeutic elements includes: hormones and hormone-agonists and antagonists, nucleic acids capable being of being used as replication, transcription, or translational templates (e.g., for expression of a protein drug having the desired biological activity or for synthesis of a nucleic acid drug as an antisense agent), enzymes, toxins, and the like.

In a preferred embodiment, the specific cell type is a pancreatic cell, most preferably a pancreatic acinar cell.

Another embodiment is drawn to methods for the treatment of acute pancreatitis comprising contacting an acinar cell with an effective amount of a composition comprising a chimeric protein containing an amino acid sequence-specific endopeptidase activity which will specifically cleave at least one synaptic vesicle-associated protein selected from the group consisting of SNAP-25, syntaxin or VAMP, in combination with the translocation activity of the N-terminus of a clostridial neurotoxin heavy chain, wherein the chimeric protein further comprises a recognition domain able to bind to a cell surface protein characteristic of an human pancreatic acinar cell. Preferably the cell surface protein is a CCK receptor protein; most preferably the protein is the human CCK A protein. CCK receptors (CCK-A receptor and CCK-B receptor) are found mainly in on the surface of pancreatic acinar cells, although they are also found in some brain cells and, to a lesser extent on the surface of gastrointestinal cells.

Any suitable route of administration may be used in this aspect of the invention. Applicants currently prefer to administer the therapeutic agent in an intravenous infusion solution; however methods such as ingestion (particularly when associated with neurotoxin-associated proteins (NAPs); see Sharma et al., *J. Nat. Toxins* 7:239–253(1998), incorporated by reference herein), direct delivery to the pancreas, injection and the like may also be used. The agent is substantially specifically targeted to pancreatic cells; when the agent contains a CCK receptor-binding domain, the blood-brain barrier prevents the agent from interacting with brain cells.

In yet another embodiment the invention provides a composition comprising a drug or other therapeutic agent having an activity other than that of a clostridial neurotoxin light chain for intracellular delivery, said agent joined to the translocation domain of a clostridial neurotoxin heavy chain and a binding element able to recognize a cell surface receptor of a target cell. In a preferred embodiment, the target cell is not a neuron. Also, in this embodiment it is preferred that the drug or other therapeutic agent has an enzymatic, catalytic, or other self-perpetuating mode of activity, so that the effective dose of drug is greater than the number of drug molecules delivered within the target cell. A non-exclusive list of certain such drugs would include: hormones and hormone-agonists and antagonists, nucleic acids capable being of being used as replication, transcription, or translational templates (e.g., for expression of a protein drug having the desired biological activity or for synthesis of a nucleic acid drug as an antisense agent), enzymes, toxins (such as diphtheria toxin or ricin), and the like.

In this embodiment the drug may be cleavably linked to the remainder of the composition in such a way as to allow for the release of the drug from the composition within the target cell.

The presently claimed compositions may be provided to the patient by intravenous administration, may be administered during surgery, or may be provided parenterally.

WO 95/32738, which shares ownership with the present application, describes transport proteins for the therapeutic treatment of neural cells. This application is incorporated by reference herein as part of this specification.

DETAILED DESCRIPTION OF THE PREFERRED EMBODIMENTS

In a basic and presently preferred form, the invention comprises a therapeutic polypeptide comprising three features: a binding element, a translocation element, and a therapeutic element.

The binding element is able to bind to a specific target cell provided that the target cell is not a motor neuron or a sensory afferent neuron. Preferably, the binding element comprises an amino acid chain; also an independently, it is preferably located at or near the C-terminus of a polypeptide chain. By "binding element" is meant a chemical moiety able to preferentially bind to a cell surface marker characteristic of the target cell under physiological conditions. The cell surface marker may comprise a polypeptide, a polysaccharide, a lipid, a glycoprotein, a lipoprotein, or may have structural characteristics of more than one of these. By "preferentially interact" is meant that the disassociation constant ($K_d$) of the binding element for the cell surface marker is at least one order of magnitude less than that of the binding element for any other cell surface marker. Preferably, the disassociation constant is at least 2 orders of magnitude less, even more preferably the disassociation constant is at least 3 orders of magnitude less than that of the binding element for any other cell surface marker to which the therapeutic polypeptide is exposed. Preferably, the organism to be treated is a human.

In one embodiment the cell surface receptor comprises the histamine receptor, and the binding element comprises an variable region of an antibody which will specifically bind the histamine receptor.

In an especially preferred embodiment, the cell surface marker is a cholecystokinin (CCK) receptor. Cholecystokinin is a bioactive peptide that functions as both a hormone and a neurotransmitter in a wide variety of physiological settings. Thus, CCK is involved in the regulation of gall bladder contraction, satiety, gastric emptying, and gut motility; additionally it is involved in the regulation of pancreatic exocrine secretion.

There are two types of CCK receptors, CCK A and CCK B; the amino acid sequences of these receptors have been determined from cloned cDNA. Despite the fact that both receptors are G protein-coupled receptors and share approximately 50% homology, there are distinct differences between their physiological activity. The CCK A receptor is expressed in smooth muscle cells of the gall bladder, smooth muscle and neurons within the gastrointestinal tract, and has a much greater affinity (>$10^2$ times higher) for CCK than the related peptide hormone gastrin. The CCK B receptor, found in the stomach and throughout the CNS, has roughly equal ability to bind CCK and gastrin.

The varied activities of CCK can be partly attributed to the fact that CCK is synthesized as procholecystokinin, a protoprotein of 115 amino acids, and is then post-translationally cleaved into a number of active fragments all sharing the same C-terminus. The amino acid sequence of human procholecystokinin is shown below; amino acid residues not present in the biologically active cleavage products are in lower case. All amino acid sequences herein are shown from N-terminus to C-terminus, unless expressly indicated otherwise:

Human procholecystokinin, having the amino acid sequence SEQ ID NO:1:

mnsgvclcvlmavlaagaltqpvppadpagsglqraeeaprrqlr VSQRT DGESRAHLGA LLARYIQQAR KAPSGRMSIV KNLQNLDPSH RISDRDYMGW MDF grrsaeeyeyps Biologically active cleavage products of the full length CCK chain include:

CCK-58, having the amino acid sequence SEQ ID NO:2:

VSQRT DGESRAHLGA LLARYIQQAR KAPSGRMSIV KNLQNLDPSH RISDRDYMGW MDF;

CCK-39, having the amino acid sequence SEQ ID NO: 3:

YIQQAR KAPSGRMSIV KNLQNLDPSH RISDRDYMGW MDF;

CCK-33, having the amino acid sequence SEQ ID NO: 4:

KAPSGRMSIV KNLQNLDPSH RISDRDYMGW MDF;

CCK-12, having the amino acid sequence SEQ ID NO: 5:

ISDRDYMGW MDF;

and CCK-8, having the amino acid sequence SEQ ID NO: 6:

RDYMGW MDF.

In each case, the biologically active polypeptides contain post-translational modifications; in the case of CCK species binding the CCK-A receptor, amidation of the C-terminal phenylalanine, and sulfatation of the tyrosine residue located seven residue from the C-terminus of the biologically active species are required for hoigh affinity binding ton the receptor. In the case of CCK-B, only the C-terminal amidation is necessary; sulfation of the tyrosine appears to make little diffrence in CCK-B binding. These modifications appear to be necessary for full biological activity, although both the unmodified C-terminal pentapeptide and tetrapeptide of CCK retains some biological activity. Kennedy et al., *J. Biol. Chem.* 272: 2920–2926 (1997), hereby incorporated by reference herein.

In a preferred embodiment, the biologically active therapeutic polypeptide of the present invention comprises a CCK binding element containing the post-translational modifications described above. This polypeptide can be produced by synthetic chemistry or, preferably, can be produced by a combination of recombinant and synthetic means using the "expressed protein ligation" (EPL) method. See Cotton & Muir, *Chemistry & Biology* 6:R247 (1999), hereby incorporated by reference herein. In this method the therapeutic polypeptide is expressed without the C-terminal binding element as a fusion protein with an "intein" polypeptide sequence positioned at the C-terminus thereof. The intein comprises a conserved cysteine, serine, or threonine residue at its amino terminus; the carboxyl terminus of the intein contains a functional binding sequence such as chitin binding domain (CBD), poly His (6 or more consecutive histidine residues), or another amino acid sequence capable of affinity binding. The coding sequence of this recombinantly expressed polypeptide is constructed using standard recombinant DNA methods.

Additionally, standard solid phase peptide synthesis methods are employed to construct a synthetic peptide comprising a C-terminal amidated phenylalanine and the desired CCK amino acid sequence. Such methods are described in e.g., Bodansky, M. and Bodansky, A. *The Practice of Peptide Synthesis* (2d ed. Trost B. M., ed. Springer Laboratory 1994), hereby incorporated by reference herein. The synthetic peptide also contains an sulfated tyrosine at the position 7 residues from the carboxyl terminus. This can be done either by incorporation of commercially available Fmoc-Tyr(OSO$_3^-$)-OH into the peptide chain at the 7$^{th}$ amino acid position prior to cleavage of the synthetic peptide from the solid support hereby incorporated by reference herein), or by standard peptide synthesis using tyrosine at position 7, followed by a sulfation reaction of the peptide resulting in tyrosine sulfate at the 7 position. See e.g., Koeller, K. M., *J. Am. Chem. Soc.* 122:742–743 (2000). The synthetic peptide is constructed with a cysteine (or serine or threonine) residue at the amino terminus.

It will be understood that one can use either hydroxyl-containing amino acids or cysteine as the amino terminal residue of the intein and the synthetic peptide, and either thiopheol, phenol or another nucleophile capable of creating a reactive ester or thioester linkage in accordance with the expressed protein ligation methods described herein. However, thiol-containing amino acid residues and thipheonol or another sulfur-containing nucleophile are preferred.

Thus, according to one embodiment of the expressed protein ligation method, the fusion protein is immobilized following expression by incubation under selective binding conditions with a surface to which the binding partner of the carboxyl terminal has been joined (e.g., where the binding moiety is CBP, the surface may be a resin to which chitin is conjugated). The immobilized fusion protein is then permitted to react in a transthioesterification reaction with a S- or O-containing reagent (such as thiophenol or phenol) and the synthetic modified peptide described above. In this step, the intein which is joined to the carboxyl terminus of the therapeutic polypeptide is cleaved at the thioester (or ester) linkage, thus liberating the protein from the surface to which it was bound. The intein may be transiently replaced with the thiophenol group, and the resulting thioester is then itself attacked by the cysteine (or serine or threonine) residue of the synthetic peptide; this reaction is then spontaneously followed by a shift of the carbonyl bond from S (or O) to the N terminal nitrogen of the synthetic peptide, to form a peptide bond. The resultant therapeutic polypeptide thus comprises a threapeutic domain, a translocation domain, and a binding domain comprising a CCK sequence modified to contain the naturally occuring post-translational modifications.

As intended herein, the term "extein" refers to a portion of a chimeric polypeptide that borders one or more intein, and is subsequently ligated to either another extein or a synthetic polypeptide in the EPL reaction referred to herein.

As intended herein, the term "intein" refers to a portion of a chimeric polypeptide containing an N-terminal cysteine, serine, or threonine which is excised from said polypeptide during the EPL reaction referred to herein.

Of course, the Applicants contemplate that this method of producing a CCK-containing therapeutic polypeptide is exemplary only, and that variations and modification of the above-described method will be well within the ability and knowledge of those of ordinary skill in the art in light of the present patent application.

While it will be understood that the applicants do not wish to be bound by theory, the following findings may assist an understanding the nature of the interaction between CCK and the CCK receptors, and thus between the CCK receptor binding element of an embodiment of the present invention and its CCK receptor target.

In pancreatic acinar cells the CCK A receptor undergoes internalization to intracellular sites within minutes after agonist exposure. Pohl et al., *J. Biol. Chem.* 272: 18179–18184 (1997), hereby incorporated by reference herein. The CCK B receptor has also shown the same ligand-dependant internalization response in transfected NIH 3T3 cells. In the CCK B receptor, but not the CCK A receptor, the endocytotic feature of the receptor been shown to be profoundly decreased by the deletion of the C terminal 44 amino acids of the receptor chain, corresponding in both receptors to an cytoplasmic portion of the receptor chain.

Recent studies of the interaction between the CCK A receptor and CCK have shown that the primary receptor sequence region containing amino acid residues 38 through 42 is involved in the binding of CCK. Residues $Trp_{39}$ and $Gln_{40}$ appear to be essential for the binding of a synthetic CCK C-terminal nonapeptide (in which the methionine residues located at residue 3 and 6 from the C-terminus are substituted by norleucine and threonine respectively) to the receptor. Kennedy et al., supra. These residues do not appear to be essential for the binding of CCK analogs JMV 180 (corresponding the synthetic C-terminal heptapeptide of CCK in which the phenylalanylamide residue is substituted by a phenylethyl ester and the threonine is substituted with norleucine), and JMV 179 (in which the phenylalanylamide residue and the L-tryptophan residues of the synthetic CCK nonapeptide are substituted by a phenylethyl ester and D-tryptophan, respectively and the threonine is substituted with norleucine). Id.

These and similar studies have shed light on the structure of the CCK A receptor active site. Based on receptor binding experiments, a current structural model indicates that CCK residues $Trp_{30}$ and $Met_{31}$ (located at positions 4 and 3, respectively, from the C terminus of mature CCK-8) reside in a hydrophobic pocket formed by receptor residues $Leu_{348}$, $Pro_{352}$, $Ile_{353}$ and $Ile_{356}$. CCK residue $Asp_{32}$ (located at amino acid position 2 measured from the C terminus of CCK-8) seems to be involved in an ionic interaction with receptor residue $Lys_{115}$. CCK Tyr-$sulfate_{27}$ (the CCK-8 residue 7 amino acids from C terminus) appears involved in an ionic interaction with receptor residue $Lys_{105}$ and a stacking interaction with receptor residue $Phe_{189}$. Ji, et al., 272 *J. Biol. Chem.* 24393–24401 (1997).

Such structural models provide detailed guidance to the person of ordinary skill in the art as to the construction of a variety of binding elements able to retain the binding characteristics of biologically active CCK peptides for the CCK-A receptor, for example, as, for example, by site directed mutagenesis of a clostridial neurotoxin heavy chain. Similarly, models deduced using similar methodologies have been proposed for the CCK B receptor, see e.g., Jagerschmidt, A. et al., *Mol. Pharmacol.* 48:783–789 (1995), and can be used as a basis for the construction of binding elements that retain binding characteristics similar to the CCK B receptor.

It will be appreciated that the CCK-B receptor is known to exist on the surface of neurons associated with the certal nervious system. In one alternative embodiment of the present invention the therapeutic polypeptide may be directed (for example, by intrathecal application) to these neurons rather than to the pancreas); in such a case, the binding element may comprise a CCK containing the C terminal amidation only. Such a binding element may be constructed using the expressed protein ligation (EPL) methods described above. Indeed, EPL methods may be used to introduce and desired or required modifications to the therapeutic element, the translocation element, and/or the binding element of the claimed therapeutic polypeptide.

Additionally, the binding element may comprise a variable region of an antibody which will bind the CCK-A or CCK-B receptor.

Nucleic acids encoding polypeptides containing such a binding element may be constructed using molecular biology methods well known in the art; see e.g., Sambrook et al., *Molecular Cloning; A Laboratory Manual* (Cold Spring Harbor Laboratory Press 2d ed. 1989), and expressed within a suitable host cell. The disclosure of this latter reference is incorporated by reference herein in its entirety.

The translocation element comprises a portion of a clostridial neurotoxin heavy chain having a translocation activity. By "translocation" is meant the ability to facilitate the transport of a polypeptide through a vesicular membrane, thereby exposing some or all of the polypeptide to the cytoplasm.

In the various botulinum neurotoxins translocation is thought to involve an allosteric conformational change of the heavy chain caused by a decrease in pH within the endosome.

This conformational change appears to involve and be mediated by the N terminal half of the heavy chain and to result in the formation of pores in the vesicular membrane; this change permits the movement of the proteolytic light chain from within the endosomal vesicle into the cytoplasm. See e.g., Lacy, et al., *Nature Struct. Biol.* 5:898–902 (October 1998).

The amino acid sequence of the translocation-mediating portion of the botulinum neurotoxin heavy chain is known to those of skill in the art; additionally, those amino acid residues within this portion that are known to be essential for conferring the translocation activity are also known.

It would therefore be well within the ability of one of ordinary skill in the art, for example, to employ the naturally occurring N-terminal peptide half of the heavy chain of any of the various *Clostridium tetanus* or *Clostridium botulinum* neurotoxin subtypes as a translocation element, or to design an analogous translocation element by aligning the primary sequences of the N-terminal halves of the various heavy chains and selecting a consensus primary translocation sequence based on conserved amino acid, polarity, steric and hydrophobicity characteristics between the sequences. The therapeutic element of the present invention may comprise, without limitation: active or inactive (i.e., modified) hormone receptors (such as androgen, estrogen, retinoid, perioxysome proliferator and ecdysone receptors etc.), and hormone-agonists and antagonists, nucleic acids capable being of being used as replication, transcription, or translational templates (e.g., for expression of a protein drug having the desired biological activity or for synthesis of a nucleic acid drug as an antisense agent), enzymes, toxins (including apoptosis-inducing agents), and the like.

In a preferred embodiment, the therapeutic element is a polypeptide comprising a clostridial neurotoxin light chain or a portion thereof retaining the SNARE-protein sequence-specific endopeptidase activity of a clostridial neurotoxin light chain. The amino acid sequences of the light chain of botulinum neurotoxin (BoNT) subtypes A-G have been determined, as has the amino acid sequence of the light chain of the tetanus neurotoxin (TeNT). Each chain contains the $Zn^{++}$-binding motif His-Glu-x-x-His (N terminal direction at the left) characteristic of $Zn^{++}$-dependent endopeptidases (HELIH of SEQ ID NO: 12 in TeNT, BoNT/A/B and /E; HELNH of SEQ ID NO: 12 in BoNT/C; and HELTH of SEQ ID NO: 12 in BoNT/D).

Recent studies of the BoNT/A light chain have revealed certain features important for the activity and specificity of the toxin towards its target substrate, SNAP-25. Thus, studies by Zhou et al. *Biochemistry* 34:15175–15181 (1995) have indicated that when the light chain amino acid residue $His_{227}$ is substituted with tyrosine, the resulting polypeptide is unable to cleave SNAP-25; Kurazono et al., *J. Biol. Chem.* 14721–14729 (1992) performed studies in the presynaptic cholinergic neurons of the buccal ganglia of *Aplysia californica* using recombinant BoNT/A light chain that indicated that the removal of 10 N-terminal or 32 C-terminal residues did not abolish toxicity, but that removal of 10 N-terminal or 57 C-terminal residues abolished toxicity in this system. Most recently, the crystal structure of the entire BoNT/A holotoxin has been solved; the active site is indicated as involving the participation of $His_{222}$, $Glu_{223}$, $His_{226}$, $Glu_{261}$ and $Tyr_{365}$. Lacy et al., supra. (These residues correspond to $His_{223}$, $Glu_{224}$, $His_{227}$, $Glu_{262}$ and $Tyr_{366}$ of the BoNT/A L chain of Kurazono et al., supra.) Interestingly, an alignment of BoNT/A through E and TeNT light chains reveals that every such chain invariably has these residues in positions analogous to BoNT/A. Kurazono et al., supra.

The catalytic domain of BoNT/A is very specific for the C-terminus of SNAP-25 and appears to require a minimum of 16 SNAP-25 amino acids for cleavage to occur. The catalytic site resembles a pocket; when the light chained is linked to the heavy chain via the disulfide bond between $Cys_{429}$ and $Cys_{453}$, the translocation domain of the heavy chain appears to block access to the catalytic pocket until the light chain gains entry to the cytosol. When the disulfide bond is reduced, the two polypeptide chains dissociate, and the catalytic pocket is then "opened" and the light chain is fully active.

As described above, VAMP and syntaxin are cleaved by BoNT/B, D, F, G and TeNT, and BoNT/$C_1$, respectively, while SNAP-25 is cleaved by BoNT/A and E.

The substrate specificities of the various clostridial neurotoxin light chains other than BoNT/A are known. Therefore, the person of ordinary skill in the art could easily determine the toxin residues essential in these subtypes for cleavage and substrate recognition (for example, by site-directed mutagenesis or deletion of various regions of the toxin molecule followed by testing of proteolytic activity and substrate specificity), and could therefore easily design variants of the native neurotoxin light chain that retain the same or similar activity.

Additionally, construction of the therapeutic agents set forth in this specification would be easily constructed by the person of skill in the art. It is well known that the clostridial neurotoxins have three functional domains analogous to the three elements of the present invention. For example, and without limitation, the BoNT/A neurotoxin light chain is present in amino acid residues 1–448 of the BoNT/A prototoxin (i.e., before nicking of the prototoxin to form the disulfide-linked dichain holotoxin); this amino acid sequence is provided below as SEQ ID NO: 7. Active site residues are underlined:

BoNT/A light chain (SEQ ID NO:7)
MPFVNKQFNYKDPVNGVDIAYIKIPNAGQMQPVKAF-KIHNKIWV IPERDTFTNPEEGDLNPPPEAKQ-VPVSYYDSTYLSTDNEKDNYLKGVTKLFERIYSTD LGRMLLTSIVRGIPFWGGSTIDTELKVIDTNCI-NVIQPDGSYRSEELNLVIIGPSADI IQFECKSF-GHEVLNLTRNGYGSTQYIRFSPDFTFGFEES LEVDTNPLLGAGKFATDPA VTLA<u>HELIH</u>AGHRL-YGIAINPNRVFKVNTNAYYEMSGLEVSFE <u>E</u>LRTFGGHDAKFIDS LQENEFRLYYYNKFKDI-ASTLNKAKSIVGTTASLQYMKNVFKEKY-LLSEDTSGKFSVD KLKFDKLYKMLTEIYTEDN-FVKFFKVLNR<u>K</u>TYLNFDKAVFKINIVPKVNYTIYD GFNL RNTNLAANFNGQNTEINNMNFTKLKNFT-GLFEFYKLLCVRGIITSKTKSLDKGYNK;

The heavy chain N-terminal ($H_N$) translocation domain is contained in amino acid residues 449–871 of the BoNT/A amino acid sequence, shown below as SEQ ID NO: 8; a gated ion channel-forming domain probably essential for the translocation activity of this peptide is underlined (see Oblatt-Montal et al., *Protein Sci.* 4:1490–1497(1995), hereby incorporated by reference herein.

ALNDLCIKVNNWDLFFSPSEDNFTNDLNKGEEI-TSDTNIEAAEENISLDLIQQYYLTFNF DNEPE-NISIENLSSDIIGQLELMPNIERFPNGKKYELDK-YTMFHYLRAQEFEHGKSRI ALTNSVNE ALLNPSRVYTFFSSDYVKKVNKATEAA-MFLGWVEQLVYDFTDETSEVSTT DKIA DITII IPYIGPALNIGNMLYKDDFVGALIFS GAVILLEFIPEIAIPVLGTFALVSYIANKVLTVQTIDN ALSKRNEKWDEVYKYIVTNWLAKVNT-QIDLIRKKMKEALENQA EATKAIINYQYNQY-TEEEKNNINFNIDDLSSKLNESINKAMINI NKFLN-QCSVSYLMN SMIPYGVKRLEDFDASLKDAL LKYIYDNRGTLIGQVDRLKDKVNNTLST-DIPFQLSKY VDNQRLLSTFTEYIK;

The heavy chain C-terminal neural cell binding domain is contained in amino acid residues 872–1296 (SEQ ID NO: 9) of the BoNT/A prototoxin.

NIINTSILNLRYESNHLIDLSRYASKINIGSKVNF-DPIDKNQI QLFNLESSKIEVILKNAIVYNSMYEN-FSTSFWIRIPKYFNSISLNNEYTIINCMENNS GWKVSLNYGEIIWTLQDTQEIKQRVVFKYSQ-MINISDYINRWIFVTITNNRLNNSKIY INGRLIDQK-PISNLGNIHASNNIMFKLDGCRDTHRYI-WIKYFNLFDKELNEKEIKDLY DNQSNSGILKD-FWGDYLQYDKPYYMLNLYDPNKYVDVNNVGIRG-YMYLKGPRGSVMTT NIYLNSSLYRGTKFIIKKYAS-GNKDNIVRNNDRVYINVVVKNKEYRLAT-NASQAGVEK ILSALEIPDVGNLSQVVV-MKSKNDQGITNKCKMNLQDNNGNDIGFIGF-HQFNNIAKLV ASNWYNRQIERSSRTLGC-SWEFIPVDDGWGERPL

The amino acid sequence of the BoNT/A prototoxin is encoded by nucleotides 358 to 4245 of the neurotoxin cDNA sequence, set forth herein below as SEQ ID NO: 10.

```
aagcttctaa atttaaatta ttaagtataa atccaaataa acaatatgtt caaaaacttg
atgaggtaat aatttctgta ttagataata tggaaaaata tatagatata tctgaagata
atagattgca actaatagat aacaaaaata acgcaaagaa gatgataatt agtaatgata
tatttatttc caattgttta accctatctt ataacggtaa atatatatgt ttatctatga
aagatgaaaa ccataattgg atgatatgta ataatgatat gtcaaagtat ttgtatttat
ggtcatttaa ataattaata atttaattaa tttttaaatat tataagaggt gttaaatatg
ccatttgtta ataaacaatt taattataaa gatcctgtaa atggtgttga tattgcttat
ataaaaattc caaatgcagg acaaatgcaa ccagtaaaag cttttaaaat tcataataaa
atatgggtta ttccagaaag agatacattt acaaatcctg aagaaggaga tttaaatcca
ccaccagaag caaaacaagt tccagtttca tattatgatt caacatattt aagtacagat
aatgaaaaag ataattattt aaagggagtt acaaaattat ttgagagaat ttattcaact
gatcttggaa gaatgttgtt aacatcaata gtaaggggaa taccattttg gggtggaagt
acaatagata cagaattaaa agttattgat actaattgta ttaatgtgat acaaccagat
ggtagttata gatcagaaga acttaatcta gtaataatag gaccctcagc tgatattata
cagtttgaat gtaaaagctt tggacatgaa gttttgaatc ttacgcgaaa tggttatggc
tctactcaat acattagatt tagcccagat tttacatttg gttttgagga gtcacttgaa
gttgatacaa atcctctttt aggtgcaggc aaatttgcta cagatccagc agtaacatta
gcacatgaac ttatacatgc tggacataga ttatatggaa tagcaattaa tccaaatagg
gttttttaaag taaatactaa tgcctattat gaaatgagtg ggttagaagt aagctttgag
gaacttagaa catttggggg acatgatgca aagtttatag atagtttaca ggaaaacgaa
tttcgtctat attattataa taagtttaaa gatatagcaa gtacacttaa taaagctaaa
tcaatagtag gtactactgc ttcattacag tatatgaaaa atgttttaa agagaaatat
ctcctatctg aagatacatc tggaaaattt tcggtagata aattaaaatt tgataagtta
tacaaaatgt taacagagat ttacacagag gataattttg ttaagttttt taaagtactt
aacagaaaaa catatttgaa ttttgataaa gccgtattta agataaatat agtacctaag
gtaaattaca caatatatga tggatttaat ttaagaaata caaatttagc agcaaacttt
aatggtcaaa atacagaaat taataatatg aatttttacta aactaaaaaa ttttactgga
```

-continued

```
ttgtttgaat tttataagtt gctatgtgta agagggataa taacttctaa aactaaatca ttagataaag gatacaataa ggcattaaat gatttatgta tcaaagttaa taattgggac ttgtttttta gtccttcaga agataatttt actaatgatc taaataaagg agaagaaatt acatctgata ctaatataga agcagcagaa gaaaatatta gtttagattt aatacaacaa tattatttaa cctttaattt tgataatgaa cctgaaaata tttcaataga aaatctttca agtgacatta taggccaatt agaacttatg cctaatatag aaagatttcc taatggaaaa aagtatgagt tagataaata tactatgttc cattatcttc gtgctcaaga atttgaacat ggtaaatcta ggattgcttt aacaaattct gttaacgaag cattattaaa tcctagtcgt gtttatacat ttttttcttc agactatgta aagaaagtta ataaagctac ggaggcagct atgtttttag gctgggtaga acaattagta tatgatttta ccgatgaaac tagcgaagta agtactacgg ataaaattgc ggatataact ataattattc catatatagg acctgcttta aatataggta atatgttata taagatgat tttgtaggtg ctttaatatt ttcaggagct gttattctgt tagaatttat accagagatt gcaatacctg tattaggtac ttttgcactt gtatcatata ttgcgaataa ggttctaacc gttcaaacaa tagataatgc tttaagtaaa agaaatgaaa aatgggatga ggtctataaa tatatagtaa caaattggtt agcaaaggtt aatacacaga ttgatctaat aagaaaaaaa atgaaagaag ctttagaaaa tcaagcagaa gcaacaaagg ctataataaa ctatcagtat aatcaatata ctgaggaaga gaaaaataat attaatttta atattgatga tttaagttcg aaacttaatg agtctataaa taaagctatg attaatataa ataaattttt gaatcaatgc tctgtttcat atttaatgaa ttctatgatc ccttatggtg ttaaacggtt agaagatttt gatgctagtc ttaaagatgc attattaaag tatatatatg ataatagagg aactttaatt ggtcaagtag atagattaaa agataaagtt aataatacac ttagtacaga tatacctttt cagctttcca aatacgtaga taatcaaaga ttattatcta catttactga atatattaag aatattatta atacttctat attgaattta agatatgaaa gtaatcattt aatagactta tctaggtatg catcaaaaat aaatattggt agtaaagtaa attttgatcc aatagataaa aatcaaattc aattatttaa tttagaaagt agtaaaattg aggtaatttt aaaaaatgct attgtatata atagtatgta tgaaaatttt agtactagct tttggataag aattcctaag tattttaaca gtataagtct aaataatgaa tatacaataa taaattgtat ggaaaataat tcaggatgga aagtatcact taattatggt gaaataatct ggactttaca ggatactcag gaaataaaac aaagagtagt ttttaaatac agtcaaatga ttaatatatc agattatata aacagatgga tttttgtaac tatcactaat aatagattaa ataactctaa aatttatata aatggaagat taatagatca aaaaccaatt tcaaatttag gtaaatattca tgctagtaat aatataatgt ttaaattaga tggttgtaga gatacacata gatatatttg gataaaatat tttaatcttt ttgataagga attaaatgaa aaagaaatca aagatttata tgataatcaa tcaaattcag gtatttttaaa agacttttgg ggtgattatt tacaatatga taaaccatac tatatgttaa atttatatga tccaaataaa tatgtcgatg taaataatgt aggtattaga ggttatatgt atcttaaagg gcctagaggt agcgtaatga ctacaaacat ttatttaaat tcaagtttgt atagggggac aaaatttatt ataaaaaaat atgcttctgg aaataaagat aatattgtta gaaataatga tcgtgtatat attaatgtag tagttaaaaa taaagaatat aggttagcta ctaatgcatc acaggcaggc
```

-continued

```
gtagaaaaaa tactaagtgc attagaaata cctgatgtag gaaatctaag tcaagtagta gtaatgaagt caaaaaatga tcaaggaata acaaataaat gcaaaatgaa tttacaagat aataatggga atgatatagg ctttatagga tttcatcagt ttaataatat agctaaacta gtagcaagta attggtataa tagacaaata gaaagatcta gtaggactt gggttgctca tgggaattta ttcctgtaga tgatggatgg ggagaaaggc cactgtaatt aatctcaaac tacatgagtc tgtcaagaat tttctgtaaa catccataaa aattttaaaa ttaatatgtt taagaataac tagatatgag tattgtttga actgccctg tcaagtagac aggtaaaaaa ataaaaatta agatactatg gtctgatttc gatattctat cggagtcaga ccttttaact tttcttgtat ccttttgta ttgtaaaact ctatgtattc atcaattgca agttccaatt agtcaaaatt atgaaacttt ctaagataat acatttctga ttttataatt tcccaaaatc cttccatagg accattatca atacatctac caactcgaga catactttga gttgcgccta tctcattaag tttattcttg aaagatttac ttgtatattg aaaaccgcta tcactgtgaa aaagtggact agcatcagga ttggaggtaa ctgctttatc aaaggttca aagacaagga cgttgttatt tgattttcca agtacatagg aaataatgct attatcatgc aaatcaagta tttcactcaa gtacgccttt gtttcgtctg ttaac
```

Of course, three distinct domains analogous to those described above for BoNT/A exist for all the BoNT subtypes as well as for TeNT neurotoxin; an alignment of the amino acid sequences of these holotoxins will reveal the sequence coordinates for these other neurotoxin species. Additionally, while sequence information is given above for BoNT/A, the amino acid sequences of all. BoNT species and tetanus toxin TeNT are known and can easily be obtained from, for example, the NCBI Gen-Bank Web site: world wide web ncbi.nlm.nih.gov. The Clostrdial neurotoxin nucleotide and amino acid sequences disclosed at this site are expressly incorporated by reference herein.

Preferably, the translocation element and the binding element of the compositions of the present invention are separated by a spacer moiety that facilitates the binding element's binding to the desired cell surface receptor. Such a spacer may comprise, for example, a portion of the BoNT $H_C$ sequence (so long as the portion does not retain the ability to bind to the BoNT or TeNT binding site of motor neurons or sensory afferent neurons), another sequence of amino acids, or a hydrocarbon moiety. The spacer moiety may also comprise a proline, serine, threonine and/or cysteine-rich amino acid sequence similar or identical to a human immunoglobulin hinge region. In a preferred embodiment, the spacer region comprises the amino acid sequence of an immunoglobulin γ1 hinge region; such a sequence has the sequence (from N terminus to C terminus):

EPKSCDKTHTCPPCP (SEQ ID NO:11)

It will be understood that none of the examples or embodiments described herein are to be construed as limiting the scope of the invention, which is defined solely by the claims that conclude this specification.

EXAMPLE 1

An agent for the treatment of acute pancreatitis is constructed as follows.

A culture of *Clostridium botulinum* is permitted to grown to confluence. The cells are then lysed and total RNA is extracted according to conventional methods and in the presence of an RNAse inhibitor. The RNA preparation is then passed over a oligo(dT) cellulose column, the polyadenylated messenger RNA is permitted to bind, and the column is washed with 5–10 column volumes of 20 mM Tris pH 7.6, 0.5 M NaCl, 1 mM EDTA (ethylenediamine tetraacetic acid), 0.1% (w/v)SDS (sodium dodecyl sulfate). Polyadenylated RNA is then eluted with 2–3 column volumes of STE (10 mM Tris (pH 7.6), 1 mM EDTA, 0.05% (w/v) SDS). The pooled mRNA is then precipitated in 2 volumes of ice cold ethanol, pelleted in a centrifuge at 10,000×g for 15 minutes, then redissolved in a small volume of STE.

The BoNT/A mRNA is used as a template for DNA synthesis using Moloney murine leukemia virus reverse transcriptase (MMLV-RT), then the L chain and then $H_N$ chain of the neurotoxin is amplified from the cDNA by the polymerase chain reaction (PCR) using appropriate oligonucleotide primers whose sequences are designed based on the BoNT/A neurotoxin cDNA sequence of SEQ ID NO: 9. These procedures are performed using the standard techniques of molecular biology as detailed in, for example, Sambrook et al., already incorporated by reference herein. The primer defining the beginning of the coding region (5' side of the L chain fragment) is given a StuI site. The PCR primer defining the 3' end of the $H_N$-encoding domain has the following features (from 3' to 5'): a 5' region sufficiently complementary to the 3' end of the HN-encoding domain to anneal thereto under amplification conditions, a nucleotide sequence encoding the human immunoglobulin hinge region $\gamma_1$ (SEQ ID NO:11), a nucleotide sequence encoding the human CCK-8 octapeptide (SEQ ID NO:6), and a unique restriction endonuclease cleavage site.

The PCR product (termed BoNT/A$^{L-HN-\gamma-CCK}$) is purified by agarose gel electrophoresis, and cloned into a pBluescript II SK vector. The resulting plasmid is used to transform competent *E. coli* cells, and a preparation of the resulting plasmid is made. The BoNT/A$^{L-HN-\gamma-CCK}$ fragment is excised from the pBluescript vector and cloned into a mammalian expression vector immediately downstream of a strong promoter. The resulting vector is used to transfect a culture of the appropriate host cell, which is then grown to confluence. Expression of the BoNT/A$^{L\text{-}HN\text{-}\gamma\text{-}CCK}$ polypeptide is induced, and the cells are lysed. The polypeptide is first purified by gel exclusion chromatography, the fractions containing the recombinant therapeutic agent are pooled, then the BoNT/A$^{L\text{-}HN\text{-}\gamma\text{-}CCK}$ polypeptide is further purified using an anti-Ig affinity column wherein the antibody is directed to the $\gamma_1$ hinge region of a human immunoglobulin.

EXAMPLE 2

Method of Treating a Patient Suffering from Acute Pancreatitis

A therapeutically effective amount of the BoNT/A$^{L\text{-}HN\text{-}\gamma\text{-}CCK}$ agent constructed and purified as set forth in Example 1 is formulated in an acceptable infusion solution. Properties of pharmacologically acceptable infusion solutions, including proper electrolyte balance, are well known in the art. This solution is provided intravenously to a patient suffering from acute is pancreatitis on a single day over a period of one to two in hours. Additionally, the patient is fed-intravenously on a diet low in complex carbohydrates, complex fats and proteins.

At the beginning of treatment, the patient's pancreas shows signs of autodigestion, as measured by blood amylase levels. After the treatment regimen, autodigestion has ceased, and the patient's pancreas has stabilized.

EXAMPLE 3

Alternative Treatment Method

In this example, a patient suffering from acute pancreatitis is treated as in Example 2, with, the therapeutic agent given continuously over a period of two weeks. After the treatment regimen, autodigestion has ceased, and the patient's pancreas has stabilized.

EXAMPLE 4

Alternative Treatment Method

In this example, a patient suffering from acute pancreatitis is given a single pharmacologically effective amount of the therapeutic agent of Example 1 by parenteral administration. Two days after the treatment regimen, autodigestion has ceased and the patient's pancreas has stabilized.

It will be understood that the present invention is not to be limited by the embodiments and examples described herein, and that the invention is defined solely by the claims that conclude this specification.

What is claimed is:

1. A composition for the treatment of acute pancreatitis in a mammal comprising, a first element comprising a binding element able to specifically bind a pancreatic acinar cell CCK receptor under physiological conditions, a second element comprising a translocation element derived from a clostridial neurotoxin heavy chain able to facilitate the transfer of a polypeptide across a vesicular membrane, and a third element comprising a therapeutic element derived from a clostridial neurotoxin light chain able, when present in the cytoplasm of a pancreatic cell, to inhibit enzymatic secretion by said pancreatic cell.

2. The composition of claim 1 wherein said therapeutic element will cleave a SNARE protein, wherein cleavage of said SNARE protein inhibits said secretion.

3. The composition of claim 2 wherein said SNARE protein is selected from the group consisting of syntaxin, SNAP-25 and VAMP.

4. The composition of claim 2 wherein said CCK receptor is the human CCK A receptor.

5. The composition of claim 4 wherein the binding element of said therapeutic polypeptide comprises a human CCK A amino acid sequence modified by the presence of a C-terminal amidated phenylalanine and a sulfated tyrosine at the position 7 residues from the carboxyl terminus.

6. The composition of claim 5 wherein said CCK A amino acid sequence comprises SEQ ID NO: 6.

7. The composition of claim 6 wherein said CCK A amino acid sequence comprises SEQ ID NO: 5.

8. The composition of claim 6 wherein said CCK A amino acid sequence comprises SEQ ID NO: 4.

9. The composition of claim 6 wherein said CCK A amino acid sequence comprises SEQ ID NO: 3.

10. The composition of claim 6 wherein said CCK A amino acid sequence comprises SEQ ID NO: 2.

* * * * *

UNITED STATES PATENT AND TRADEMARK OFFICE
CERTIFICATE OF CORRECTION

PATENT NO.   : 6,843,998 B1
DATED        : January 18, 2005
INVENTOR(S)  : Steward et al.

It is certified that error appears in the above-identified patent and that said Letters Patent is hereby corrected as shown below:

Column 1,
Line 35, delete "juiced" and insert in place thereof -- juice --

Column 10,
Line 38, delete "$Phe_{189}$" and insert in place thereof -- $Phe_{198}$ --

Column 17,
Line 35, delete "all." and insert in place thereof -- all --

Signed and Sealed this

Thirty-first Day of May, 2005

JON W. DUDAS
*Director of the United States Patent and Trademark Office*